United States Patent
Bonnet et al.

(10) Patent No.: US 8,301,575 B2
(45) Date of Patent: Oct. 30, 2012

(54) METHOD AND DEVICE FOR THE RECOGNITION OF THE POSITION OR MOVEMENT OF A DEVICE OR A PERSON

(75) Inventors: Stephane Bonnet, Seyssinet (FR); Christelle Godin, Brignoud (FR)

(73) Assignee: Commissariat a l'Energie Atomique, Paris (FR)

( * ) Notice: Subject to any disclaimer, the term of this patent is extended or adjusted under 35 U.S.C. 154(b) by 1133 days.

(21) Appl. No.: 12/178,559

(22) Filed: Jul. 23, 2008

(65) Prior Publication Data
US 2009/0030345 A1    Jan. 29, 2009

(30) Foreign Application Priority Data
Jul. 23, 2007 (FR) .................................. 07 56683

(51) Int. Cl.
*G06F 15/18* (2006.01)
(52) U.S. Cl. ........... 706/12; 706/924; 600/545; 600/595
(58) Field of Classification Search ............. 706/12
See application file for complete search history.

(56) References Cited

U.S. PATENT DOCUMENTS

| | | | |
|---|---|---|---|
| 6,658,287 B1* | 12/2003 | Litt et al. | 600/544 |
| 6,735,467 B2* | 5/2004 | Wilson | 600/544 |
| 6,889,129 B2* | 5/2005 | Suzuki et al. | 701/45 |
| 8,190,251 B2* | 5/2012 | Molnar et al. | 600/545 |
| 2002/0103610 A1* | 8/2002 | Bachmann et al. | 702/94 |
| 2008/0294315 A1* | 11/2008 | Breed | 701/49 |
| 2009/0030345 A1* | 1/2009 | Bonnet et al. | 600/587 |
| 2009/0062696 A1* | 3/2009 | Nathan et al. | 600/595 |
| 2009/0099627 A1* | 4/2009 | Molnar et al. | 607/62 |
| 2010/0280574 A1* | 11/2010 | Carlson et al. | 607/59 |
| 2010/0280579 A1* | 11/2010 | Denison et al. | 607/62 |
| 2011/0060252 A1* | 3/2011 | Simonsen et al. | 600/595 |

(Continued)

FOREIGN PATENT DOCUMENTS
WO    2005094676 A1    10/2005

OTHER PUBLICATIONS

Becq et al. Collection and exploratory analysis of attitude sensor data in an epilepsy monitoring unit, Proceedings of the 29th annual international conference of IEEE EMBS, France, 2007, pp. 2775-2778.*

(Continued)

*Primary Examiner* — Jeffrey A Gaffin
*Assistant Examiner* — David H Kim
(74) *Attorney, Agent, or Firm* — Nixon Peabody LLP

(57) ABSTRACT

This method uses two sets of sensors to estimate certain characteristics of the movement of a device or a person or states, especially postures, they adopt. A first, abundant, set of sensors (1) is removed after a learning phase where it records with certainty the states obtained by interpreting first decisional rules. The measurements of a second set of sensors (2), much more restricted than the first, are correlated to the states reached during the learning period by second decisional rules automatically obtained by supplying a classifier. They are then interpreted to determine the new states reached by the wearer just by means of the second sensors. The results are good in spite of the low number of second sensors, thanks to the accuracy of the second decisional rules.

10 Claims, 2 Drawing Sheets

U.S. PATENT DOCUMENTS

2012/0029390 A1* 2/2012 Colborn ............... 600/595
2012/0053491 A1* 3/2012 Nathan et al. ........... 600/595
2012/0108998 A1* 5/2012 Molnar et al. .......... 600/545

OTHER PUBLICATIONS

Guillaume Becq, Stéphane Bonnet, Lorella Minotti, Michel Antonakios, Régis Guillemaud, Philippe Kahane, Classification of epileptic motor manifestations using inertial and magnetic sensors, Computers in Biology and Medicine, vol. 41, Issue 1, Jan. 2011, pp. 46-55.*

Fahrenberg, Jochen et al., "Assessment of Posture and Motion by Multichannel Piezoresistive Accelerometer Recordings," Psychophysiology, 34, 1997, Cambridge University Press, pp. 607-612.

International Search Report, Application No. 08159980.5, dated Aug. 14, 2008.

Marins, Joao L. et al., "An Extended Kalman Filter for Quaternion-Based Orientation Estimation Using MARG Sensors," Proceedings of the 2001 IEEE/RSJ, International Conference on Intelligent Robots and Systems, 2001 pp. 2003-2011.

Veltink, Peter H. et al, "Detection of Static and Dynamic Activities Using Uniaxial Accelerometers," IEEE Transactions on Rehabilitation Engineering, vol. 4, No. 4, Dec. 1996, pp. 375-385.

* cited by examiner

METHOD AND DEVICE FOR THE RECOGNITION OF THE POSITION OR MOVEMENT OF A DEVICE OR A PERSON

CROSS REFERENCE TO RELATED APPLICATIONS OR PRIORITY CLAIM

This application claims priority to French Patent Application No. 07 56683, filed Jul. 23, 2007.

DESCRIPTION

The purpose of this invention is a method and a device for the recognition of the position or movement of a device or a person, in order to recognise events which occur during the movement, and which may be either movement phases or static states reached during the movement, such as the physical postures of a person.

There are many applications. From them we may mention the recognition of handwritten characters from the movement of a pen or medical surveillance to identify abnormal states of a person, likely to indicate an accident or a fit, such as an epileptic fit.

More particularly, we study methods where sensors are attached to the device or the person to be observed and the movements or the position are measured. They comprise two main types. In the first type, there is a large number of sensors positioned on the device or the person, and the combination of their measurements allows the information sought to be deduced directly, possibly in graph form. These methods are simple to use and are efficient to determine a physical posture, however the use of multiple sensors has an intrusive nature that is unpleasant for a person wearing them.

In another type of method, a single sensor, or more generally a single group of sensors, is used, fitted together on a same set-up, or possibly a small number of sensors positioned on the device or the person. The measurements taken are in this case insufficient in number to provide immediately the information sought on the movement (direction, intensity, etc.) or the position (orientation, distance to a fixed reference, etc.) and need to be interpreted by data rules that are either arbitrary or taken from a learning phase during which the device or the person is observed and the measurements recorded by the sensors are correlated to the states reached identified by the observer. The application of the rules then permits the reappearance of states identified during the learning phase to be diagnosed when measurements identical to the corresponding states are observed. Such rules are even more suitable when conditions are favourable, especially when the movements are repetitive or there are not very many different states reached or are very characterised, which permits easier classifications to be made. They may fail however, either by providing incorrect results if they have not been established accurately or concern a new movement, or if they tolerate uncertainties if they do not have sufficient details. Some uncertainties may be intrinsic to the system used: in this case it is impossible to distinguish an immobile standing position from a seated position by orientation sensors or accelerometers fixed to the torso by simply considering the corresponding static state. If these second methods with a reduced number of sensors are quite suited for measuring the intensity of a movement (actimetry), they need to be perfected to make them more efficient for finer studies of movements and positions reached in order to recognise the posture of the wearer and then the nature of the activity or occupation (posturometry).

One purpose of the invention is therefore to perfect this second type of method, using a small number of sensors worn at a small number of measurement points by the device or the person, often at a single point, to classify events successfully, such as the postures of the wearer when learning is complete.

This invention relates to a method for the recognition of the position or movement of a device or a person, comprising the following steps: providing first and second sets of sensors on or close to the device or person; measuring, during a learning phase, the readings recorded by the sensors and applying first predefined decisional rules at least to the measurements taken by the first set of sensors to classify each event identified using the measurements of all or part of the sensors into a position or movement category; creating a learning base, during the learning phase, identifying for all or part of said events their pre-established classification and the characteristics from the measurements of the second set of sensors; defining second decisional rules based on the learning base permitting an event to be classified based on measurements taken by the second set of sensors; removing the first set and only keeping the second set of sensors on the device or the person; and classify the position or the movement of the device or person, in a recognition phase, by applying the second decisional rules to the measurements made by the second set of sensors.

The method of the invention may be applied to the recognition of postures and movements, wherein the first and second sets of sensors comprise movement sensors such as accelerometers, magnetometers and gyrometers.

According to one embodiment of the above-mentioned method, the first set of sensors comprises accelerometers fitted to the thighs and legs of the wearer.

According to one embodiment of the above-mentioned method, the second set of sensors comprises a tri-axial magnetometer and a tri-axial accelerometer fitted to a wearer, for example on the torso.

According to one embodiment of the above-mentioned methods, the classified events comprise standing, seated and lying down postures as well as transitions between said standing, seated and lying down postures.

The method of the invention may also be applied to the recognition of epileptic fits, wherein the first set of sensors comprises a sensor for the electrical activity of the brain of a person wearing the sensors, and the second set of sensors fitted to the wearer comprises movement sensors such as accelerometers, magnetometers and gyrometers.

The method of the invention may also be applied to the recognition of epileptic fits, wherein the first set of sensors comprises an image recording device, and the second set of sensors fitted to the wearer comprises movement sensors such as accelerometers, magnetometers and gyrometers.

Furthermore, the method of the invention may be applied to the recognition of handwritten characters, wherein the first set of sensors is a graphic pad connected to sign identification means and the second set of sensors comprises movement sensors mounted on a pen.

According to one embodiment of one of the above-mentioned methods, the method comprises driving a neurone system with the learning base to draft the second decisional rules.

The invention further provides a device to apply one of the above-mentioned methods, which comprises the first set of sensors and the second set of sensors, and means of processing the measurements provided by the sensors containing a learning base and an adjustable classifier.

The invention will now be described in relation to the figures, in which.

Figure 1:
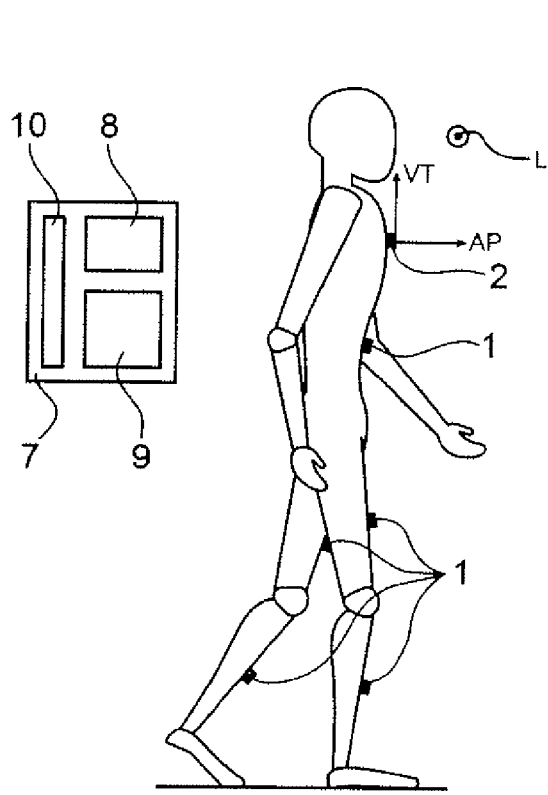
FIG. 1 illustrates a first application.

The description first relates to FIG. 1. The invention is based on the use of two sets of sensors, including a second set of sensors or second sensors 2 concentrated at a single measurement point and comprising, in the embodiment of FIG. 1, a tri-axial accelerometer and a tri-axial magnetometer or a gyrometer, and a first set of sensors or first sensors 1 especially comprising accelerometers which are positioned at a relatively high number of measurement points. In one common application of the study of human movements, illustrated in FIG. 1, the second sensors 2 may be fitted to the torso, and the first sensors 1 for example on the thighs and shins, or on other regions of the torso.

In this embodiment as in the others, the system comprises a computer 7 which collects the measurements from all of the sensors 1 and 2 and comprises a learning base 8 as well as a classifier 9 and an element 10 to interpret the results provided by the classifier 9 that is suited to the aims of the method (recording memory for the movements and states, graphic interface, alarm system, etc).

The recognition method according to the invention may be broken down into two main phases: a learning phase and a recognition phase. During the learning phase, the movements made by the person studied, to whom the first and second sets of sensors 1 and 2 are fitted, monitored and analysed. During the recognition phase, the position or the type of movement made by the person is defined by using just the second set of sensors, as the first set of sensors have been removed.

During the learning phase, the measurements provided by the various sensors 1 and 2 are transmitted to the computer 7. The classifier 9 then uses all or part of the measurements provided by the sensors 1 and 2 to determine with a high confidence level the postures or movements of the person wearing the sensors 1 and 2. To achieve this, the classifier 9 uses the pre-defined first decisional rules. For example, the standard first decisional rules could be used which only use the measurements provided by the various accelerometers of the first and second sets of sensors 1 and 2. It may be noted that the use of the measurements provided by the second sensors is optional for determining the classification.

Examples of first decisional rules may be found in the following articles:

Article by P. H. Veltink, H. B. J Bussmann, W. de Vries, W. L. J. Martens and R. C. van Lummel, entitled "Detection of static and dynamic activities using uniaxial accelerometers", IEEE Trans. Rehab. Eng., vol 4, n° 4, pages 375-385, December 1996;

Article by G. M. Lyons, K. M. Culhane, D. Hilton, P. A. Grace and D. Lyons, entitled "A description of an accelerometer-based mobility monitoring technique", Medical Engineering and Physics, vol. 27, pages 497-504, 2005;

U.S. Pat. No. 6,834,436 by Microstrain Inc, entitled "Posture and body movement measuring system".

In the example of FIG. 1, the classifier is used to attribute a classification (for example Seated, Standing, Lying down, Seated-lying down Transition, Seated-standing Transition, etc.) to each event detected from the measurements of the sensors. To determine these successive events and attribute a classification, the classifier may directly use the measurements of the sensors or calculate the values of various parameters (mean value, energy etc.) from the measurements of the sensors.

Preferably, only the measurements of the second sensors will be used to identify the successive events, which is to say to "slice" temporally the signals received into a sequential succession of events. Once this sequential succession of events has been defined, the measurements of the first sensors and possibly all or part of the second sensors are used to attribute a classification to each previously identified event. An example of an embodiment of such a method for identifying and classifying events is provided in the following description.

Progressively as the classifications of events are made by the classifier, the learning base 8 is automatically enriched with new data. Consequently, for each classification of an event made by the classifier 9, a new item of data is added to the learning base. Each new item of data comprises "characteristics" obtained from measurements provided by the second set of sensors 2 and the corresponding classification indicated by the classifier 9. The term "characteristics" means one or several values corresponding either to a measurement of one of the sensors of the set of sensors 2 or to a calculated value, defined from all or part of the measurements provided by the second set of sensors 2. Examples of characteristics that may be used as part of the recognition of a posture or movement of a person are the duration of the event considered, the leaning of the person in a given plane, "laced" values of the torso corresponding to a mean orientation with respect to the magnetic North and to a mean deviation with respect to this mean orientation of a signal from a magnetometer on the duration of the event considered, and the energy of an acceleration signal.

This learning base the permits a classifier such as a neurone system to be trained by a supervised learning method and to determine second optimal rules for the classification of postures to be applied to the signals from the second sensors 2.

The learning phase may be stopped when there is sufficient data, when it may be considered that the second rules have been established with sufficient accuracy. It is possible to accomplish this by testing on a portion of the learning base, called validation base that is not used to create the second rules.

It may be observed that the second classification rules, which are implicit and adjusted flexibly, are adapted to express the specific aspects of the movements of wearer and the surrounding environment.

In the recognition periods following the learning period, the first sensors 1 are removed and the wearer only keeps the second sensors 2. Their signals are extracted and transmitted to the classifier 9, which applies the second decisional rules.

Figure 5:
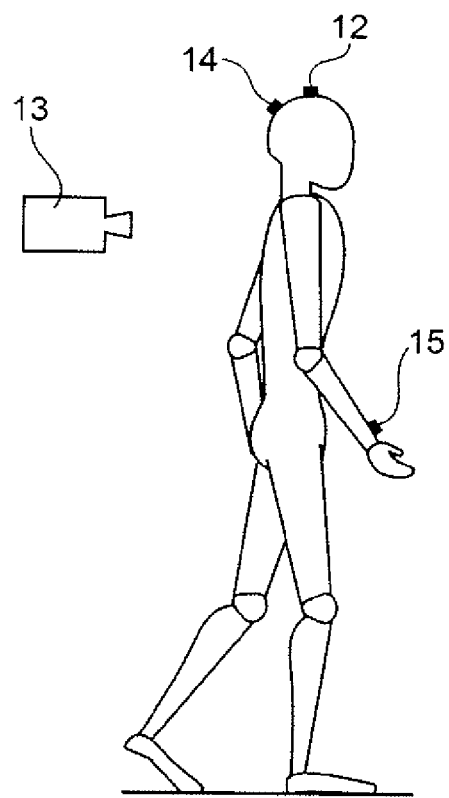
FIG. 5 illustrates a third application.
Figure 4:
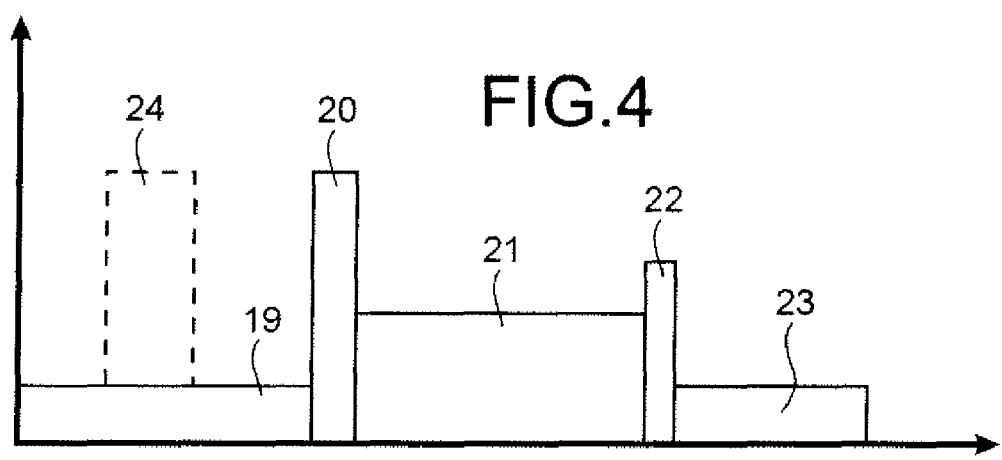
FIG. 4 is a diagram of a signal division.

One example of the determination of a sequence of events that may be used as part of the recognition of a posture or movement of a person as well as an example of a detailed classification are provided below. Based on the signals from the sensors 2, a characteristic called the activity energy is evaluated, an example of which is shown in FIG. 4. In order to define a sequence of events, "pre-classification" decisional rules are applied to distinguish between certain types of activity of the person and certain of the person's postures. In the diagram of FIG. 4, expressed in activity energy in function of time, there are successively a standing state, a standing/seated transition, a seated state, a seated/standing transition and a standing state in states 19 to 23. The transition states always correspond to strong activities and energy peaks, and the stable position states are often longer and less active, but exceptions exist, such as running, wherein the wearer in the stable standing position will have a high energy level. Furthermore, the energy may vary considerably within a same state. A running period 24 in the first standing state 19 is thus shown. It is therefore not possible to deduce directly the succession of states of a diagram such as that of FIG. 5, but it allows a rational division into segments of unequal duration of homogenous characteristics.

Consequently, the recording of the "energy activity" characteristic is broken down into temporal portions or segments according to a set of several criteria. This consequently provides an alternation of homogenous zones in the sense of the postures (called "O-segments") and active zones ("1-segments") which potentially represent postural transfers. Each temporal segment designates an event.

A classification of each event is then made using the measurements from the sensors 1 and possibly all or part of the sensors 2. For information, there can be nine classes of static or dynamic posture: three stable states (seated, standing and lying down), and six states where there is a transfer from one of the previous stable states to another (standing to seated, seated to standing, standing to lying down, lying down to standing, seated to lying down and lying down to seated).

Figure 3:
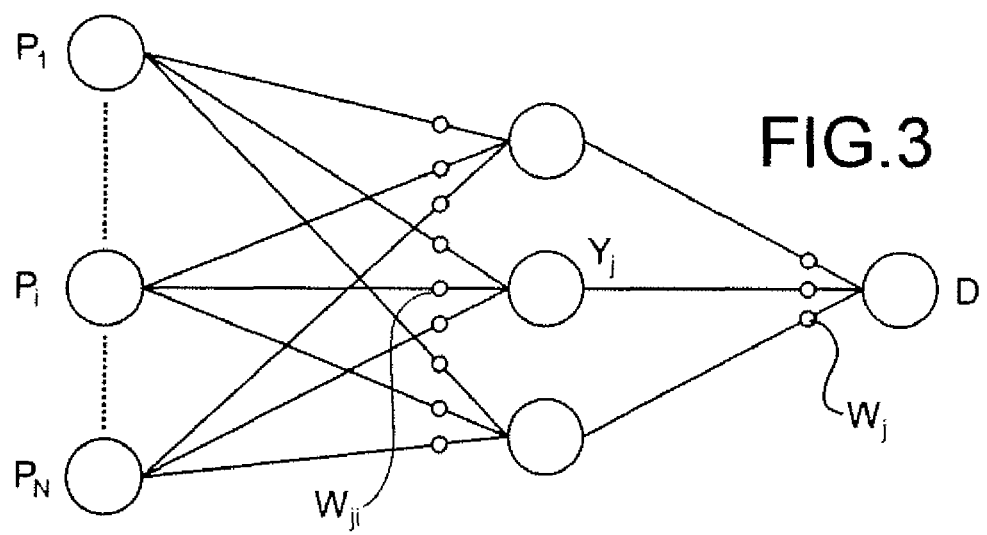
FIG. 3 illustrates a neurone network.

The use of a neurone system in FIG. 3 is described below, as an example of a classifier capable of applying the second decisional rules. The system comprises a layer of input neurones P1, P2, etc., Pn to receive the values of the characteristics of the signals from the second sensors 2 in numerical form.

The decision to classify in a determined class is provided, also in numerical form, by the contents of an output neurone D. The neurone system comprises at least one hidden layer of neurones $y_j$ which makes numerical combinations of the parameters and transmits them to the next layer of the system, in this case immediately to the output neurone D. Numerical weightings w are applied to the values transmitted before they reach the neurones of the hidden layer or the output neurone. In this case, the neurones of the hidden layer make a hyperbolic tangential activation and the output neurone makes a linear activation. The decision function may the be written according to the formula (1)

$$D_W(\overline{P}) = \text{sgn}\left(\sum_j w_j \tanh\left(\sum_i w_{ji} p_i + w_{0j}\right) + w_o\right) \quad (1)$$

where sgn is the sign function, tanh the hyperbolic tangential function, $w_j$ the weighting connecting the output from the neurone $y_j$ to the output neurone D, $w_0$ and $w_{0j}$ are specific weightings called bias or thresholds connecting a fictive output neurone with a value equal to 1 to the output neurone (for $w_0$) or to the neurones $y_j$ of the hidden layer (for $w_{0j}$) and $w_{ji}$ are the weightings connecting the input neurones $P_i$ to the neurones of the hidden layer $y_j$.

The neurone systems permit, on the condition that the number of neurones in the hidden layer or hidden layers is chosen correctly, any function to be approached once the correct weightings have been identified. Drafting the second decisional rules therefore means adjusting the weightings w so as to coincide, for each example or almost in the learning base, the result of the decision by the neurone system and the result, know from the first rules, of the classification. In the learning phase, a computer associated to the system adjusts the weightings so that the largest number of events in the learning base is evaluated correctly by the second decisional rules. It may be observed that this adjustment of the weightings permits the automatic modelling of the second decisional rules to perfect them.

Other types of numerical classifiers are known from the prior art: linear separators, with wide margins, decision trees, SVM (support vector machine); the invention also applies to them.

The characteristics used to adjust the classifier are directly calculated on the signals acquired by the second sensors 2 or on the derived signals (lean angle, laced angle, activity index, etc.). The characteristics calculated are for example, for each segment:
- the statistics on the signals,
- the duration,
- the frequency content (distribution of the energy peaks in the frequency field),
- even the segment itself (signature), Other types of sensors may be used, such as gyrometers or physiological activity sensors of the wearer. The first set of sensors may be fitted to a different measurement point, such as the back or the belt, or even positioned in a small number of measurement points on the wearer. The states recognised by the system may be not only static postures but the transfers from one posture to another, Another concrete application of the invention consists in monitoring epileptic patients (FIG. 5) by means of simple monitoring devices such as movement sensors.

During a learning period, a first set of sensors is placed on or close to the patient. The first set of sensors may consist of a sensor for the electrical activity of the brain 12 of the patient and/or a video camera 13 which records the activity. A sensor for the electrical activity of the brain 12 consists of a set of electrodes implanted or fitted to the surface of the brain and connected to a system for recording the electrical activity of part of the brain. In this learning phase, second set of sensors 2 is also placed on the patient designed to record the movements of part of the patient's body. This second set of sensors may be composed of accelerometers, magnetometers and/or gyrometers 14 or 15 worn on the head or the wrists of the patient. This second set is designed to detect the characteristics movements of a fit such as shaking, slow rotations of the head or the arms, etc.

The sensors 1 and 2 are connected to a computer such as that shown in FIG. 1 which comprises a learning base 8, a classifier 9 and an interpreting element 10.

In this learning phase, the video camera 13 or the electrical activity sensor 12 is used to determine the presence or absence of a fit. Finally, the aim is to identify two classes of events, which is to say the "fit" and "non-fit" classes.

The learning base is built as follows. A series of events is identified from the measurements from the movement sensors 14, 15 (second set of sensors). By event, it is meant a rotation of the head, shaking of the wrist, etc. A given "fit" or "non-fit" classification is associated to all or part of these identified events, wherein this classification is made by the classifier 9 based on the signals from the first set of sensors 12 and/or 13. Each event/classification association forms a new item of data that is recorded in the learning base 8.

At the end of this learning phase, or progressively as it is carried out, second classification rules are defined, from the learning base, which will be used by the classifier 9 in the evaluation phase (monitoring phase). The classifier that may implement these second classification rules may again be a neurone system.

The first sensors are then removed and the following fits will be diagnosed using just the second sensors, wherein the second decisional rules permit the normal activity to be distinguished from the epileptic activity.

Contrary to the monitoring devices of the prior art which permanently use a video camera or a sensor for the electrical activity of the brain, the invention permits epileptic fits to be detected using less intrusive devices that may be used anywhere and not solely in a room equipped with a video camera. The following articles may be referred to. For the use of electrical activity sensors, the article by N. C. Bhavaraju, M. G. Frei and I Osorio may be referred to, entitled "Analog Seizure Detection and Performance Evaluation", IEEE Trans. On Biomedical Eng., vol. 53, n° 2, February 2006. For the use of a video camera, the article by Nicolaos B. Karayiannis et al may be referred to, entitled "Automated Detection of Videotaped Neonatal Seizures of Epileptic Origin", Epilepsia, 47(6):966-980, 2006.

Figure 2:
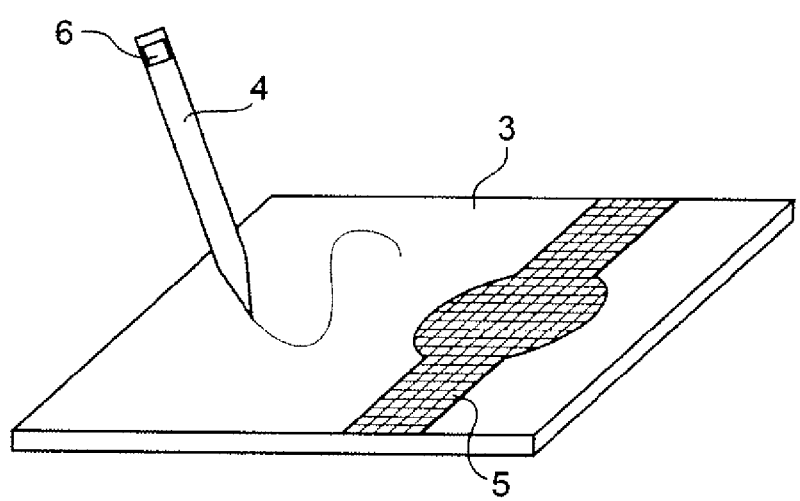
FIG. 2 illustrates a second application.

Another embodiment of the invention will now be described in relation to FIG. 2. This concerns the recognition of handwritten characters as they are written. In a learning phase, a graphic pad 3 is used (which exists, called Flybook) equipped with writing sensors underneath its surface, forming a first set of sensors 5, and an algorithm for recognising characters that are written on it, wherein this algorithm uses first decisional rules. A pen 4 equipped with a second set of sensors 6 is used to write on the graphic pad 3, wherein these sensors may consist of accelerometers, magnetometers, gyrometers or force sensors. The creation of the learning base consist, for a certain number of letters or written words, in recognising them via the graphic pad 3, and correlating them to the measurements made by the second set of sensors 6 on the pen 4. In the following recognition phase, where the graphic pad 3 is removed, the measurements of the second set of sensors 6 are used to identify the characters marked onto any support directly.

Consequently, as we have seen, if the most common sensors are contact sensors, fixed to the device or to the person that is the subject matter of the method, the invention does not exclude remote sensors positioned in front of the person, which record the person's movement or other parameters by means of an image, a distance or other parameters.

Furthermore, the computer used in the examples of embodiments of the above-mentioned invention may be replaced by any type of means for processing the measurements provided by all or part of the sensors. For example, a computer may be used in the learning phase, then simply a portable processing device placed on the device or the person whose positions or movements are to be monitored. Similarly, the connection between the sensors and the processing means may be by wire or wireless.

The invention claimed is:

1. Method for the recognition of the position or movement of a device or a person, comprising the following steps:
   providing first and second sets of sensors (1, 2, 5, 6, 12, 13, 14, 15) on or close to the device or person;
   measuring, during a learning phase, the readings recorded by the sensors and applying first predefined decisional rules at least to the measurements taken by the first set of sensors to classify each event identified using the measurements of all or part of the sensors into a position or movement category;
   creating a learning base, during the learning phase, identifying for all or part of said events their pre-established classification and the characteristics from the measurements of the second set of sensors;
   defining second decisional rules based on the learning base permitting an event to be classified based on measurements taken by the second set of sensors;
   removing the first set of sensors (1, 6, 12, 13) and only keeping the second set of sensors (2, 5, 14, 15) on the device or the person; and
   classifying the position or the movement of the device or person, in a recognition phase, by applying the second decisional rules to the measurements made by the second set of sensors.

2. Method according to claim 1, characterised in that it is applied to the recognition of postures and movements, wherein the first and second sets of sensors comprise movement sensors such as accelerometers, magnetometers and gyrometers.

3. Method according to claim 2, characterised in that the second set of sensors comprises a tri-axial magnetometer and a tri-axial m accelerometer fitted to a wearer.

4. Method according to claim 3, characterised in that the first set of sensors comprises accelerometers fitted to the thighs and legs of the wearer.

5. Method according to claim 2, characterised in that the classified events comprise standing, seated and lying down postures as well as transitions between said standing, seated and lying down postures.

6. Method according to claim 1, characterised in that it is applied to the recognition of epileptic fits, wherein the first set of sensors comprises a sensor for the electrical activity of the brain of a person wearing the sensors, fitted to the wearer comprises movement sensors such as accelerometers, magnetometers and gyrometers.

7. Method according to claim 1, characterised in that it is applied to the recognition of epileptic fits, wherein the first set of sensors comprises an image recording device, and the second set of sensors fitted to the wearer comprises movement sensors such as accelerometers, magnetometers and gyrometers.

8. Method according to claim 1, characterised in that it is applied to the recognition of handwritten characters, wherein the first set of sensors is a graphic pad connected to sign identification means and the second set of sensors comprises movement sensors mounted on a pen.

9. Method according to claim 1, characterised in that it comprises driving a neurone system with the learning base to draft the second decisional rules.

10. Device for the application of a method for the recognition of a position or movement of an object or a person, comprising following steps:
   providing first and second sets of sensors (1, 2, 5, 6, 12, 13, 14, 15) on or close to the object or person;
   measuring, during a learning phase, the readings recorded by the sensors and applying first predefined decisional rules at least to the measurements taken by the first set of sensors to classify each event identified using the measurements of all or part of the sensors into a position or movement category;
   creating a learning base, during the learning phase, identifying for all or part of said events their pre-established classification and the characteristics from the measurements of the second set of sensors;
   defining second decisional rules based on the learning base permitting an event to be classified based on measurements taken by the second set of sensors;
   removing the first set of sensors (1, 6, 12, 13) and only keeping the second set of sensors (2, 5, 14, 15) on the object or the person; and
   classifying the position or the movement of the object or person, in a recognition phase, by applying the second decisional rules to the measurements made by the second set of sensors,
   characterised in that it comprises the first set of sensors and the second set of sensors, and means of processing the measurements provided by the sensors containing a learning base and an adjustable classifier.

* * * * *